(12) United States Patent
Olsson et al.

(10) Patent No.: US 6,811,751 B1
(45) Date of Patent: Nov. 2, 2004

(54) METHOD AND APPARATUS FOR DETERMINING INDIRECTLY THE CONCENTRATION OF A SPECIFIC SUBSTANCE IN THE BLOOD

(75) Inventors: Sven Gunnar Olsson, Arlov (SE); Stefan Brauer, Lund (SE); Anders Linge, Kavlinge (SE); Tarmo Niininen, Hoor (SE); Krista Nilsson, Malmo (SE); Goran Rydgren, Bunkeflostrand (SE)

(73) Assignee: Servotek AB, Arlov (SE)

( * ) Notice: Subject to any disclaimer, the term of this patent is extended or adjusted under 35 U.S.C. 154(b) by 0 days.

(21) Appl. No.: 09/297,798
(22) PCT Filed: Nov. 6, 1997
(86) PCT No.: PCT/SE97/01854
 § 371 (c)(1),
 (2), (4) Date: Apr. 11, 2002
(87) PCT Pub. No.: WO98/20346
 PCT Pub. Date: May 14, 1998

(30) Foreign Application Priority Data

Nov. 6, 1996 (SE) .............................................. 9604059

(51) Int. Cl.[7] .............................. G01N 31/00
(52) U.S. Cl. ...................... 422/84; 422/83; 422/86; 436/62; 436/68; 436/127; 436/164; 436/133
(58) Field of Search ............................. 422/83; 436/62, 436/68, 127, 164

(56) References Cited

U.S. PATENT DOCUMENTS 3,785,774 A   1/1974  Murphy
4,314,564 A   2/1982  Albarda
4,671,298 A   6/1987  Babb et al.
5,376,555 A  12/1994  Forrester et al.
5,458,853 A  10/1995  Porter et al.
5,531,225 A * 7/1996  Nawata et al. .............. 600/532

FOREIGN PATENT DOCUMENTS

WO        8702773        5/1987

OTHER PUBLICATIONS

American Journal of Public Health, vol. 83, No. 4, Apr. 1993, Robert D. Foss, PhD et al., Using a Passive Alcohol Sensor to Detect Legally Intoxicated Drivers, p. 556—p. 560—p. 557.
Clinical Science, vol. 63, 1982, A.W. Jones, Effects of temperature and humidity of inhaled air on the concentration of ethanol in a man's exhaled breath, p. 441—p. 445.

* cited by examiner

Primary Examiner—Robert J. Warden, Sr.
Assistant Examiner—Sam P. Siefke
(74) Attorney, Agent, or Firm—James Ray & Associates

(57) ABSTRACT

Method and apparatus for determining in a person's exhalation air the concentration of a specific substance in the blood by measuring the concentration of said substance and the concentration of water vapor in the exhalation air and utilizing a known relationship between these concentrations. When the method is applied the exhalation air is exhaled freely in a defined air volume having a predetermined composition, and said concentrations are measured in this air volume. The apparatus for working the method comprises a device (16) which defines a space for receiving the exhalation air, which has two mutually opposite openings through which the space communicates with the surrounding air, and means (18, 22, 23) for selective quantitative detection of said substance in the air in the defined space.

6 Claims, 5 Drawing Sheets

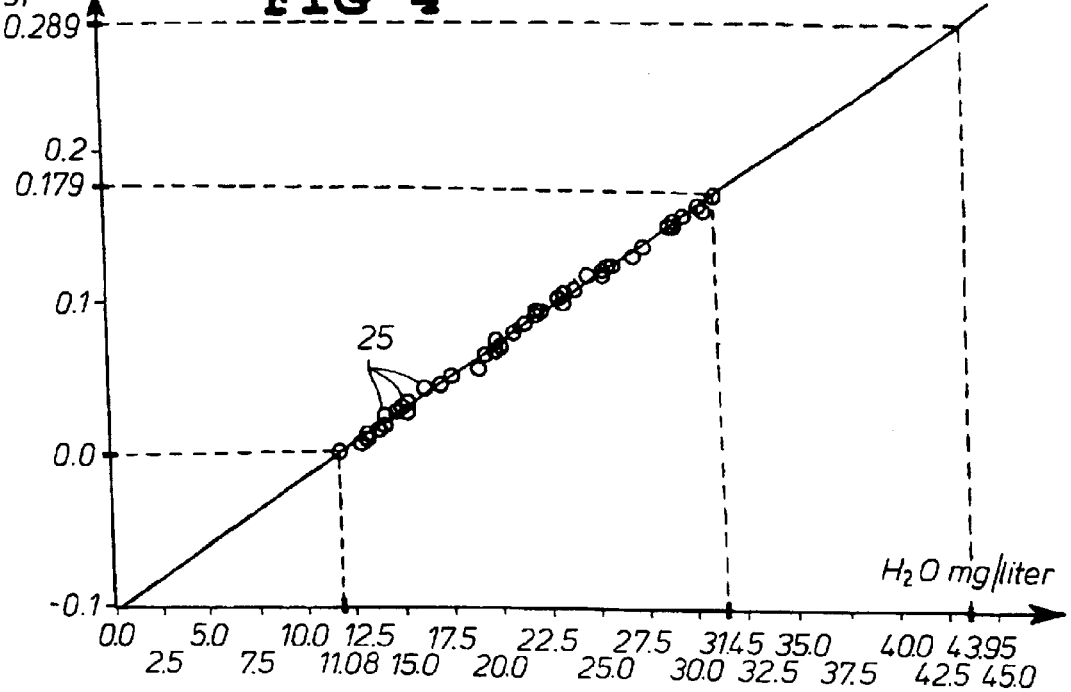
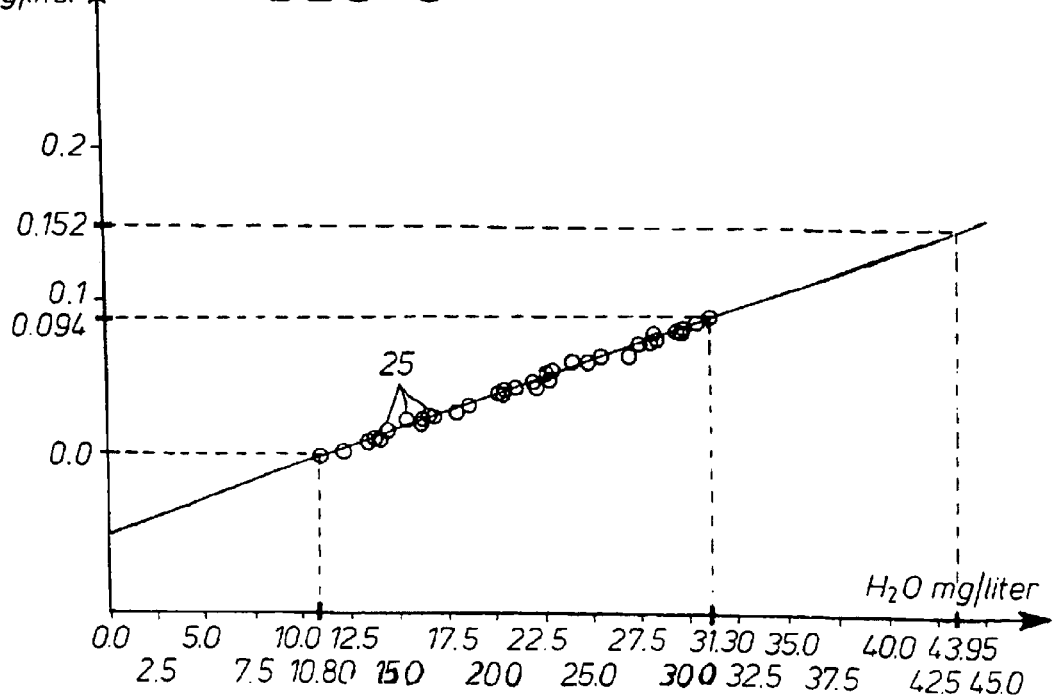

METHOD AND APPARATUS FOR DETERMINING INDIRECTLY THE CONCENTRATION OF A SPECIFIC SUBSTANCE IN THE BLOOD

The invention relates to a method for determining indirectly the concentration of a predetermined substance in the blood by measuring the concentration of said substance and the concentration of water vapour in a person's exhalation air and utilizing a known relationship between these concentrations.

The method according to the invention is proposed particularly for determining alcohol concentration but can be applied also for determining the concentration of other substances which may occur in the blood.

U.S. Pat. No. 4,314,564 describes such a method for determining alcohol concentration and also an apparatus for working the method, exhalation taking place directly into a tube from one end thereof via a mouthpiece. When one and the same apparatus shall be used for performing sequential alcohol tests on several different persons the mouthpiece must be exchangeable for hygienic reasons so there is used a disposable mouthpiece for each person being tested, which is an economic burden when using the apparatus for mass tests the mouthpiece exchange at each test also requiring attendance and making performance of the test more lengthy. Moreover, the necessity of the person to be tested placing the mouthpiece against the lips means that the test hardly can be performed without attracting public attention, which in specific situations may be rather annoying to the person being tested.

U.S. Pat. No. 5,376,555 describes method and device for determining the concentration of alveolar alcohol in exhalation air blown into an infrared sensing device. The presence of alcohol from the respiratory tract of the person being tested is detected by continuously monitoring alcohol and carbon dioxide, normalizing alcohol values with respect to carbon dioxide, calculating a difference between normalized alcohol concentration and carbon dioxide concentration over time, integrating the difference, and comparing the integrated difference with a threshold value. The alcohol concentration in the blood cannot be determined in a reliable manner by this method because the carbon dioxide content in the exhalation air is not constant but varies from one breath to another and also during the breath.

In the most common method according to prior art technique for determining the alcohol concentration in the blood of a person, for example in a traffic control a breathing test is performed wherein the alcohol concentration at the end of a deep exhalation is measured. In that case the maximum alcohol concentration in the alveolar air (that part of the exhalation air which has been deepest in the lung) is measured. Since the exact temperature in the lung is unknown and accordingly also the temperature at which the alcohol has been evaporated is unknown there will be an error in the determination of the blood alcohol content, which amounts to about 7%/° C. deviation. The lung temperature may vary several degrees in dependence of the body temperature (fever), the outside temperature, breathing pattern, body strain etc., and the error may be considerable. By measuring the temperature of the exhaled alveolar air one can partly compensate for this error but since the temperature recrease from the lung to the point of measuring will be great and will vary with breathing pattern, the outside temperature etc. the remaining error also in this case will be considerable.

U.S. Pat. No. 5,458,853 describes a device for analyzing a breath sample particularly for determining if a driver is under the influence of alcohol or not. The device allows sampling by two different methods: in one sampling method the test person is exhaling towards an inlet port, and in the other sampling method the person is exhaling through a mouthpiece. The first-mentioned sampling method constitutes "passive" sampling and is effected very discretely without manual operations. By this sampling those persons can be screened off who have no alcohol at all in the blood. These persons undergo no further sampling while the persons who turn out to have alcohol in the blood for a more accurate determination of the alcohol content undergo sampling according to the other method which requires use of a mouthpiece which for hygienic reasons must be exchanged after each sampling. In the "passive" sampling the exhalation can comprise an entirely common exhalation so that measuring can be effected on persons who exhale freely and entirely normally. In other words, no special breathing technique is required for performing the test. As a consequence thereof the test can be performed very discretely without the test being noticed by people closest to the tested person or even by this person himself. Accordingly a screening test on several persons can be sequentially effected without the necessity of taking manual measures at each individual test such as exchange of a mouthpiece or another article of consumption. The sampling is performed in a hygienic way and moreover in a way which is experienced as minimally offending the personal integrity.

The device according to U.S. Pat. No. 5,458,853 is proposed in the first place for the police department's "flying" control of the soberness of drivers and aims at reducing, for the purpose of saving costs, the use of mouthpieces but there are many other situations wherein it is desired to automatically and rapidly effect unattended alcohol tests in a "passive" manner for example alcohol tests on visitors to a public entertainment when the visitors pass an entrance, alcohol tests on drivers at payment sites on toll roads and at garage exits, and alcohol tests on employees at working places where alcohol problems exist among the personnel, i.e. situations where it is desired to screen off more or less drunken persons. Another example of a passive alcohol test is when a person serves a sentence at home provided with an electronic foot shackle in order to check that the sentenced person satisfies the requirement of refraining from alcohol.

"American J. Public Health, volume 83(4), pages 556–560, (1993)" discloses the use of the CMI/MPH Alcolmeter VAS in field studies for passive alcohol testing. However, the design of the said meter is not disclosed therein.

"Clinical Science, volume 63, pages 441–445, (1982)" discloses that there is a relation between temperature, humidity and alcohol concentration in exhaled air from persons with alcohol in the blood. The alcohol concentration was determined by a gas chromatograph attached to a mouthpiece.

The object of the invention is to make possible that the concentration of a specific substance in the blood is indirectly determined by "passive" measurement of the concentration of said substance in a person's exhalation air with greater accuracy than can be achieved in prior art methods and devices by minimizing the error which is dependent on variation of the evaporation temperature (lung temperature) and even with greater accuracy than can be achieved by active devices wherein exhalation takes place through a mouthpiece and a special breathing technique and the tested person's complete participation is required.

A further object of the invention is to make possible that the measurement is performed rapidly by the tested person exhaling freely without special breathing technique being required for performing a reliable measurement.

In order to achieve these objects it is proposed according to the invention a method for determining indirectly the concentration of a specific substance in the blood of the kind referred to above having the characterizing features of claim 1.

The invention also provides an apparatus for working the method according to claim 11.

The concentration of alcohol in the exhalation air is dependent not only of the alcohol concentration in the 30 blood but also—in the same manner as the concentration of water vapour—of the lung temperature. The change of the saturation pressure, in dependence of the temperature is different for water and alcohol, respectively, but the difference is small. If 37° C. is chosen as a normal temperature the error in the measurement when applying the method according to the invention will be a deviation of about 0.9%/° C. from the normal temperature, which should be compared with the accuracy of about 7%/° C. achieved when applying prior art technique.

In order to eliminate also this error in the measurement of about 0.9%/° C. which is low per se there is proposed according to claim 20 also a modification of the method according to the invention wherein the test person exhales through a mouthpiece at one end of a defined flow passage in order that the concentration of said specific substance and the concentration of water vapour shall be determined by measuring the undiluted alveolar gas, and the deviation of the evaporation temperature from a normal temperature can be determined for correction in determining the content of the specific substance in the blood.

In order to explain the invention in more detail two illustrative embodiments of the apparatus according to the invention and the manner in which the method according to the invention is applied by using these apparatuses will be described below reference being made to the accompanying drawings in which FIG. 1 is a diagrammatic axial cross sectional view of the apparatus according to the invention in one embodiment thereof;

FIG. 4 is a diagram showing the relationship between alcohol and water in the exhalation air from a person;

FIG. 5 is a diagram showing the relationship between alcohol and water in the exhalation air from a person having a lower alcohol content in the blood than the person in FIG. 4;

Figure 1:
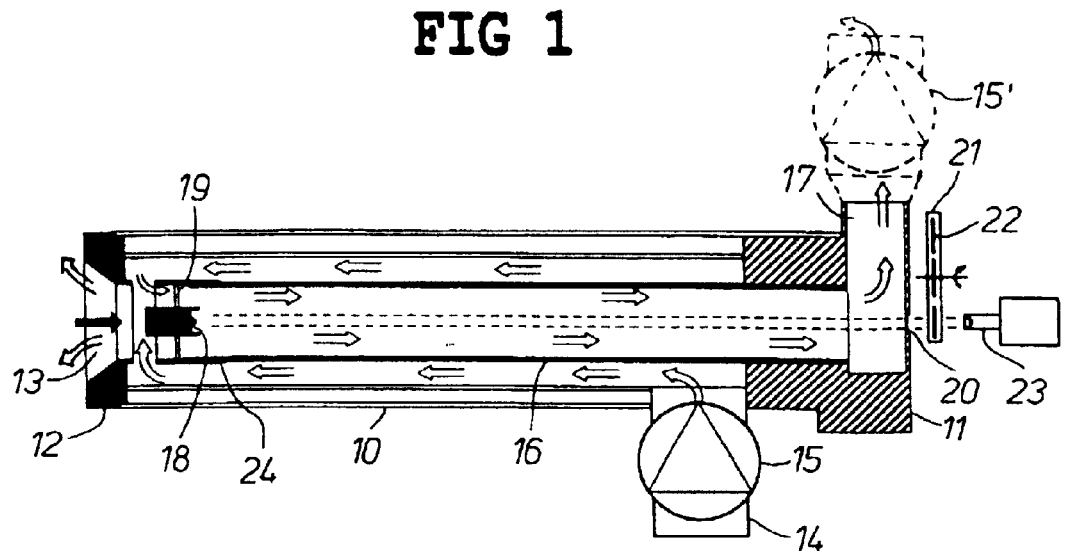
Figure 2:
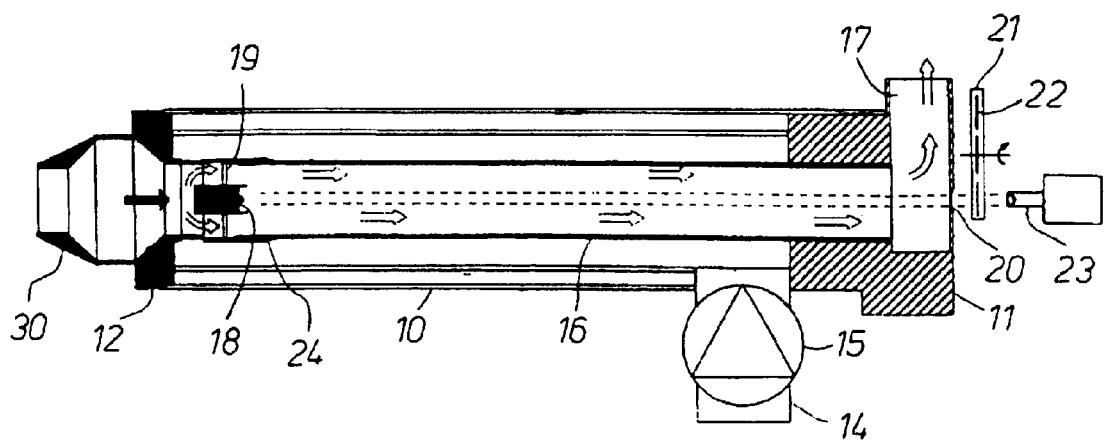
FIG. 2 is a diagrammatic view similar to FIG. 1 but with the apparatus provided with a mouthpiece for applying the modified method according to the invention.
Figure 3:
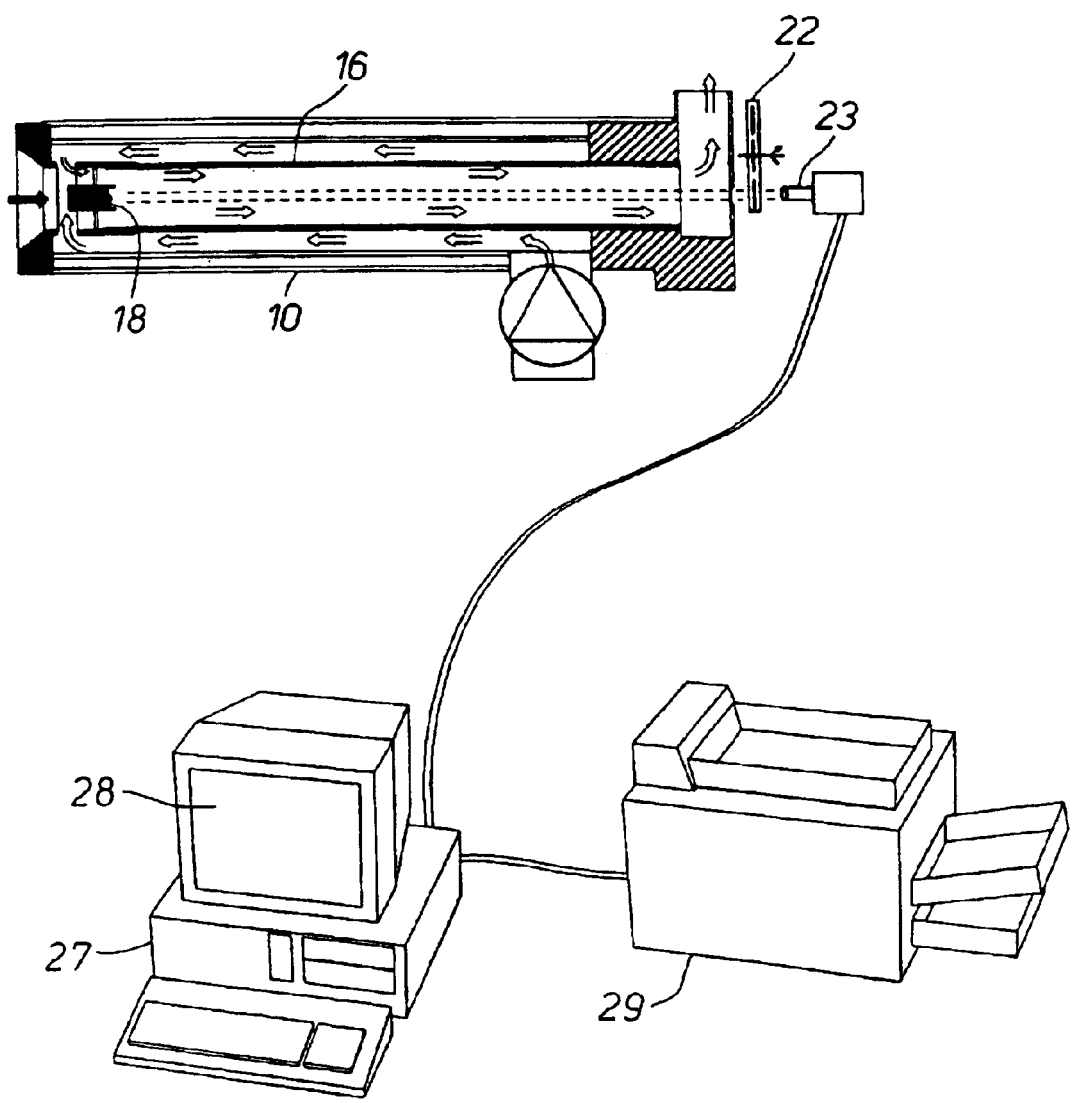
FIG. 3 is a view of the apparatus connected with a computer and a printer.

The apparatus according to the invention is principally a gas analyzer and comprises in the first embodiment according to FIGS. 1 to 3 a double-walled cylindrical cuvette 10 having a heat insulating air gap between the outer wall and the inner wall. The cuvette is closed at one end thereof by means of an end element 11 while it is open towards the surroundings at the other end where the cuvette is provided with a rim 12 forming a funnel-shaped inlet opening 13 of the cuvette. A conduit 14 having a fan or air pump 15 or a flask with pressurized air connected to the conduit opens radially in the cuvette adjacent the end element 11. A cylindrical inner tube 16 is mounted coaxially inside the cuvette said inner tube having an open end thereof axially spaced from the air inlet 13 and being attached at the other end thereof to the end element 11 where it communicates with a transverse passage 17 in the end element.

A radiation source 18 is supported in said open end of the inner tube 16 by means of one or more radial wings 19 which do not substantially block the passage through the inner tube. A window 20 is mounted in the end element 11 in register with the radiation source. Outside the end element a filter wheel 21 having in this case four filters 22 is mounted for rotation about an axis which is parallel with the axes of the cuvette 10 and the inner tube 16, by means of an electric motor, not shown, in order that the filters 22 shall be brought one after the other to a position in register with the window 20. A light detector 23 is mounted at the side of the filter wheel opposite to the window in register with the radiation source 18 and the window 20 as well as the filter 22 at the time in register with the window. In case the apparatus is intended for alcohol test three of the filters are for alcohol, water, and carbon dioxide measurement, respectively, while the fourth filter is a reference filter. A thermostatically controlled electric heating element 24 is mounted to the inner tube 16.

When the apparatus described is being used the conduit 14 should be in connection with a space wherein the air is free from the gas the concentration of which in the exhalation air shall be measured in the apparatus, or the air has a known concentration of this gas and moreover has a known concentration of water. The air in this space is drawn in by the fan or air pump 15 either directly or via a zeolit or coal filter for equalization of the content of said gas and water vapour. The air is transported into the annular space between the cuvette 10 and the inner tube 16 and flows in this space towards the open end of the cuvette where the air partly escapes to the surroundings through the inlet opening 13 in the rim 12 while the rest of the air is deviated by the rim towards the open end of the inner tube 16 to flow through this tube into the outlet passage 17 and arrive from there at the surroundings. The air flow is indicated by contoured arrows. The person to be tested by using the apparatus directs his or hers exhalation air towards the inlet opening 13 without having the lips in contact with the rim 12. An air jet which consists of a free air flow in the room but is not necessarily sharply defined is emitted from the mouth at a distance from the inlet opening towards this opening during a completely common exhalation and is directed into and through the inlet opening 13, which has been marked by a solid arrow, in order then to flow through the inner tube 16 together with the air supplied from the conduit 14 the inner tube being kept at a predetermined elevated temperature by means of the heating element 24 preferably at 40° C., in order to avoid condensation in the inner tube. A light beam is emitted from the radiation source 18, preferably infrared light, axially through the inner tube 16, and this light beam passes through the window 20 in order then to be captured by the detector 23 via one of the filters 22 in the rotating filter disc 21 the detector sensing the light intensity which can be used for determining the concentration of a specific substance in the air passing through the inner tube depending on the filter which at time is located in the beam passage.

The method of the invention is based on the fact that there is a relationship between the concentration of a gas existing in the exhalation air, the concentration of which in the blood shall be determined indirectly, and another gas existing in the exhalation air said gas preferably consisting of water vapour in the special case of determining the concentration of alcohol. Due to the large contact surface (larger than 70 m²) between the breathing gas and the alveolar walls the breathing gas always will be saturated with water vapour at the actual vaporization temperature (lung temperature). At the normal lung temperature of 37° C. the concentration of water vapour is 43.95 mg/l. The relationship between the concentration of water vapour and the concentration of alcohol is substantially linear. Therefore, it is not necessary for measuring the concentration of alcohol in the exhalation air to measure a complete exhalation; it is sufficient to determine the concentration of water vapour and the concentration of alcohol in the exhalation air at one or more shorter but not too small exhalations in order to obtain the linear relationship between said two concentrations and then on the basis of this relationship determine the concentration of alcohol at the end of a complete exhalation of a person at normal temperature (37° C.).

By measuring the content of carbon dioxide in the exhalation air the exhalation can be safely defined in order to secure that the measurement result indeed refers to exhalation air. For this purpose the measurement of concentration of water vapour and the concentration of alcohol is started first at a measured predetermined value of the carbon dioxide content in the exhalation air.

The coordinate system in FIG. 4 to which reference now is made the abscissa indicates the concentration of water in the exhalation air from a person in mg/l while the ordinate indicates the concentration of alcohol in the exhalation air, also in mg/l. A number of short exhalations have been made and the intersections of the measured concentrations of water and alcohol have been marked in the coordinate system at small circles 25. It will be seen that in these intersections are located substantially on a straight line 26 which has been obtained by drawing a line through the lowest intersection located at the water concentration 11.08 mg/l and the alcohol concentration 0 mg/l, and the highest intersection which is located at the water concentration 31.45 mg/l and the alcohol concentration 0.179 mg/l. Since the relationship between the water and alcohol concentrations follow this line it can be read from the shown diagram that the alcohol content at the end of an exhalation at 43.95 mg/l water is 0.289 mg/l. Since it is known that an alcohol concentration of 0.47 mg/l corresponds to an alcohol content in the blood of 1.0‰, the alcohol content in the blood at the measurement shown in the diagram according to FIG. 4 is 0.62‰. The diagram in FIG. 4 relates to measurement at normal temperature (37° C.) but as mentioned above the error at a deviation from the normal temperature will be only a deviation of 0.9%/° C.

FIG. 5 discloses a corresponding diagram as that in FIG. 4 for a person having a lower alcohol content in the blood than the person in the example in FIG. 4. In this case the line 26 indicating the relationship between the water concentration and the alcohol concentration in the exhalation air, is drawn through a lowest point representing 10.8 mg/l water and 0 mg/l alcohol in the exhalation air, and a highest point representing 31.30 mg/l water and 0.094 mg/l alcohol in the exhalation air. At the end of an exhalation corresponding to a water concentration in the exhalation air of 43.95 mg/l the alcohol concentration in the exhalation air is 0.152 mg/l corresponding to an alcohol concentration in the blood of 0.32‰.

When the method according to the invention is applied it is not necessary that the exhalations are deep but the accuracy of the measurement will be greater at deeper exhalations due to existing "noise".

When the person being tested has mouth alcohol the measurement points will not be located on a straight line but on a non-linear curve which initially rises steeply then to turn downwards. Such test results therefore can be easily excluded, which is an advantage not existing in known measurement devices. Another advantage of the method according to the invention is that it does not allow faking of the measurement result by mixing exhalation air with another gas.

The apparatus of FIG. 1 can be supplemented with a further fan or air pump 15' which is connected to the passage 17 and is shown by dotted lines in FIG. 1. This pump can be used when measuring on a person who is unconscious and therefore cannot himself or herself blow into the tube 16. In such measurement the apparatus is turned with the inlet opening 13 towards the face of the person, and while the air pump 15' is inoperative the air pump 15 is operated in order to flood the face of the person with air taken in through the conduit 14. Then, the air pump 15 is stopped and the air pump 15' is started in order to draw exhalation air from the person through the tube 13 and to measure in the manner described above.

For working the method according to the invention by using the analysis apparatus described the detector 23 is, according to FIG. 3, via matching electronics connected to a computer 27 having a screen 28 which shows the measuring result, for processing the output signals of the detector. A printer 29 is connected to the computer for printing out the measurement result so that the person tested can get the test verified. The measurement procedure and the necessary mathematic calculations in order to obtain a value of the alcohol concentration in the blood is controlled by a program installed in the computer. As mentioned above the filter wheel 21 has in addition to filters for measuring the water and alcohol concentrations also two further filters one of which shall comprise a filter for measuring the concentration of carbon dioxide in the exhalation air and the other one shall comprise a reference filter, i.e. a filter for measuring "noise" existing in the apparatus so that during the computer processing compensation can be made for such noise, and drift and influence on the measurement result by other substances which may exist in the breathing air can be eliminated. In the computer processing also other factors affecting the measurement can be taken into account such as air pressure and air temperature. The carbon dioxide measurement can be used for starting the measurement procedure as mentioned above. Further filters can be provided on the filter wheel for measuring the concentration of other substances than those mentioned herein, which may exist in the exhalation air, or for filtering out substances having an absorption similar to that of alcohol for example methyl alcohol.

The measurement method described herein can be used in order to perform a screening test for determining if a person has an alcohol content in the blood which is higher than a predetermined value, and such a screening test can be performed discretely without any attendance for example for mouthpiece exchange, and in short time. At the measurement there remains as mentioned above an error which is a deviation of about 0.9%/° C. from normal lung temperature. In order to eliminate also this error the apparatus according to the invention can be used with a mouthpiece as shown in FIG. 2. The mouthpiece indicated at 30 fits in the rim 12 and is pushed into the inner tube 16. In this case the person to be tested thus shall blow into the mouth-piece which projects from the apparatus, and only the exhalation air, no supplementing air flow, passes through the inner tube 16 in order to measure the exhalation air in the manner described above. In other respects the measurement is performed in the manner described above but since the exhalation air in this case is blown directly into the inner tube the concentration will be measured directly in the undiluted alveolar gas. Before the mouth-piece is inserted into the apparatus this can be rinsed with air supplied via the conduit 14, and be calibrated with a gas of known composition.

Figure 6:
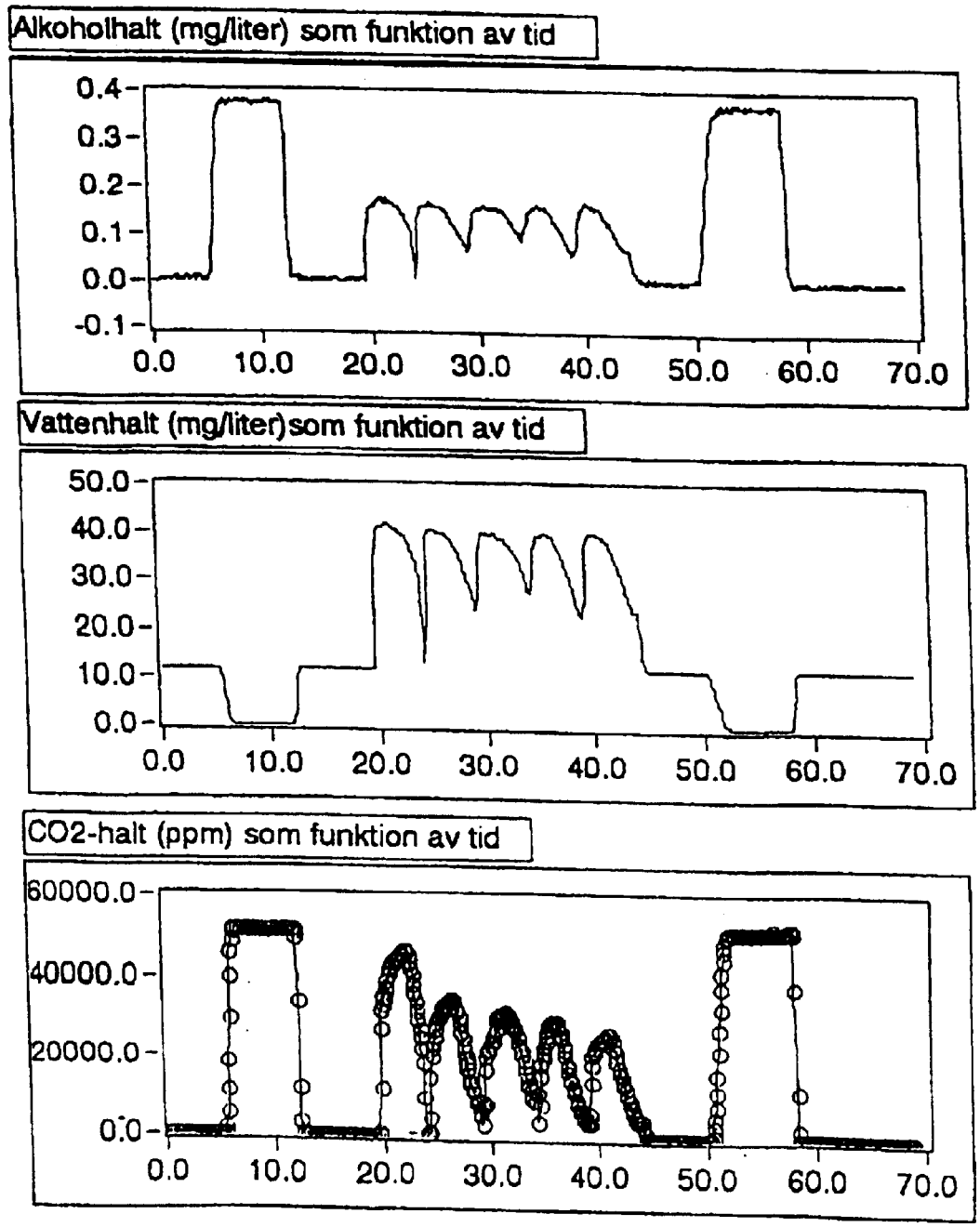
FIG. 6 shows registered measurement values for alcohol, water, and carbon dioxide from a breathing test.

FIG. 6 discloses registered measurement values from a breathing test wherein the apparatus was first calibrated with a reference gas and the person then breathed five times into the analyzer. The test was terminated by blowing the reference gas again into the analyzer in order to secure that the prerequisites of the test had not changed during the testing. In the uppermost diagram the alcohol in the exhalation air is shown in mg/l as a function of the time. The middle diagram discloses the water content in the exhalation air in mg/l as a function of the time. As has been described above the relationship between the alcohol content and the water content is linear the measurement values forming a straight line according to the examples in FIGS. 4 and 5. Finally, in the lowermost diagram in FIG. 6 the carbon dioxide content in the exhalation air is shown in ppm as a function of the time. Thus, the apparatus measures the alveolar concentration of alcohol, and from the water vapour measurement the exact evaporation temperature can then be calculated and the blood alcohol concentration thus can be determined without any temperature dependent error. By the registration of these diagrams it is verified that the test is correctly performed and that the apparatus used functions in a correct way, which means that the legal security is high in case the test shall be used as evidence in connection with drunken driving etc.

Figure 7:
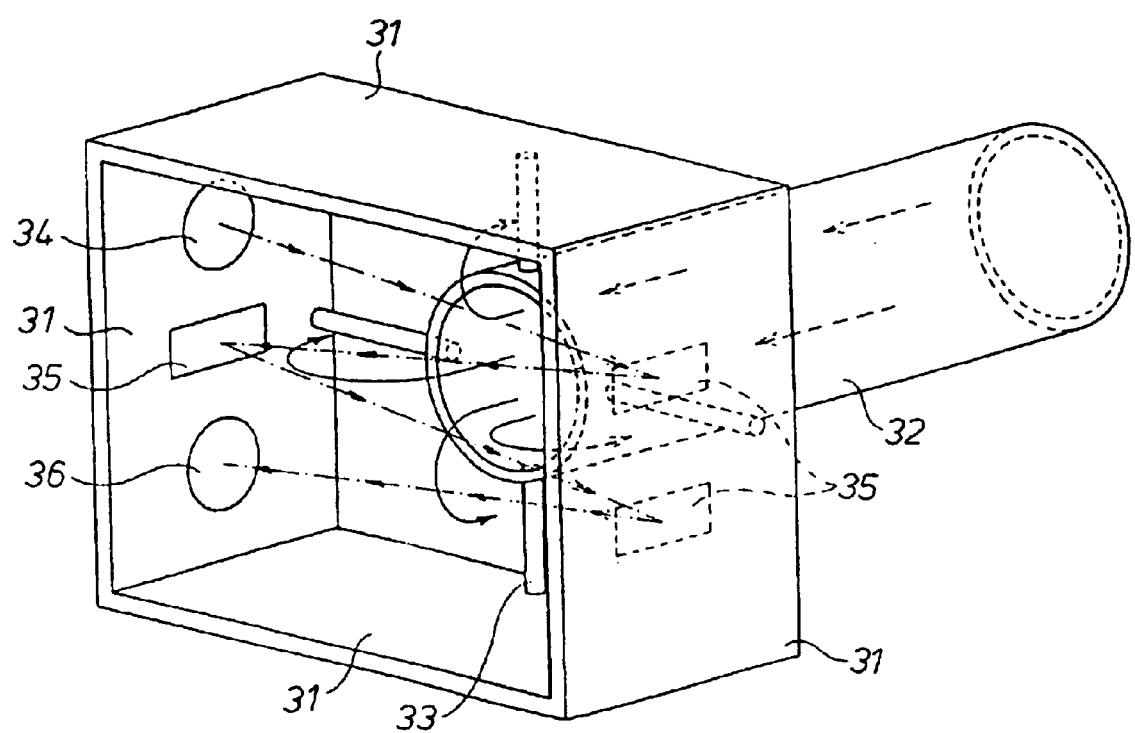
FIG. 7 is a diagrammatic perspective view of the apparatus according to the invention in a second embodiment thereof.

The embodiment of the apparatus according to the invention shown in FIG. 7 is particularly well suited for discrete, passive, unattended alcohol tests. The apparatus comprises a construction having four side walls 31 defining a parallelepipedic space which is open at two opposite sides. In one open side a tube 32 is supported by a spider 33 attached to the side walls, and this tube shall be connected to a fan or compressor for supply of a constant or intermittent air flow to the defined parallelepipedic space. A light source 34 for example for infrared light is provided in one of two opposite side walls 31, and the light beam emitted therefrom is reflected by mirrors 35 on these side walls towards a detector 36 which is mounted on the same side wall as the light source. The detector is in a manner not shown in detail herein provided with filters as described in connection with the first embodiment of the apparatus according to the invention. The detection of the presence of water vapour and alcohol (or another substance) as well as the processing of the output signals of the detector takes place in the manner described above.

The construction which defines the space can be so large that people can pass through the space and thus will exhale therein but it can also have smaller dimensions and be located in such a manner that a person when performing a specific action for example payment of road toll, purchase of an entrance ticket, or time-recording at the working place, has the face turned towards the defined space in register with one of the openings and exhales into the space. The detector can be connected in order to control a door, a turnstile, or a bar, so that the door will not be opened or will remain locked, the turnstile will remain latched, or the bar will not be lifted in case the indicator senses an alcohol content above a predetermined value.

As mentioned above the invention is not limited to the determination of the alcohol content in the blood but can be used also for determining indirectly the concentration of other substances in the blood for example the concentration of ammonium, which can indicate specific diseases, the concentration of anaesthetics after narcoses, or the concentration of solvents used in some technical processes.

What is claimed is:

1. Apparatus for determining in a person's exhalation air the concentration of a specific substance in the blood by measuring the concentration of said substance and the concentration of water vapor in the exhalation air and utilizing a known relationship between said concentrations, comprising a tube which defines a space for receiving exhalation air, the tube being open at both ends for exhalation air flow from one end to the other, said space communicating with the surrounding air through the open ends thereof, means for selective quantitative detection of said substance in the air in the defined space, a cuvette which is open at one end thereof, said tube being mounted coaxially in the cuvette said one end of the tube being located axially inwardly of the open end of the cuvette and means connected to an annular gap defined between the tube and the cuvette for supplying air to said gap which communicates with the tube at said one end thereof, and an inlet allowing free exhalation into said space at said one end of the tube and allowing air supplied to said gap to escape partly through said inlet flushing the face of a person exhaling into said space.

2. Apparatus according to claim 1 further comprising means for supplying an air flow through one of said open ends of the tube.

3. Apparatus according to claim 1 wherein the gap communicates also with said one end of the cuvette.

4. Apparatus according to claim 3 further comprising means connected to said other end of the tube for drawing exhalation air through the tube, these means as well as said means for supplying air to the gap being alternatingly operative.

5. Apparatus according to claim 3 wherein said one end of the cuvette is provided with a rim defining an injection opening and is constructed to deviate the air supplied through the gap, towards said one end of the tube.

6. Apparatus according to claim 1 wherein said means for selective quantity detection comprises a radiation source at said one end of the tube for emission of a light beam axially through the tube, and a detector with filters at said other end of the tube.

\* \* \* \* \*